(12) United States Patent
Lantz et al.

(10) Patent No.: US 10,016,255 B2
(45) Date of Patent: Jul. 10, 2018

(54) DENTAL SURGERY DEVICE

(71) Applicant: Elos Medtech Timmersdala AB, Timmersdala (SE)

(72) Inventors: Mattias Lantz, Mariestad (SE); Per-Olof Karlsson, Alingsås (SE)

(73) Assignee: Elos Medtech Timmersdala AB, Timmersdala (SE)

( * ) Notice: Subject to any disclaimer, the term of this patent is extended or adjusted under 35 U.S.C. 154(b) by 0 days.

(21) Appl. No.: 14/911,014

(22) PCT Filed: Aug. 25, 2014

(86) PCT No.: PCT/SE2014/050968
§ 371 (c)(1),
(2) Date: Feb. 8, 2016

(87) PCT Pub. No.: WO2015/030653
PCT Pub. Date: Mar. 5, 2015

(65) Prior Publication Data
US 2016/0184051 A1 Jun. 30, 2016

(30) Foreign Application Priority Data
Aug. 26, 2013 (SE) ...................................... 1350974

(51) Int. Cl.
*A61C 1/08* (2006.01)
*A61C 3/02* (2006.01)
(Continued)

(52) U.S. Cl.
CPC ........ *A61C 1/084* (2013.01); *A61B 17/32053* (2013.01); *A61C 1/082* (2013.01);
(Continued)

(58) Field of Classification Search
CPC ........... A61C 1/084; A61C 1/082; A61C 3/02; A61C 8/0089; A61B 17/32053; A61B 17/1673; A61B 2017/320052
(Continued)

(56) References Cited

U.S. PATENT DOCUMENTS

| 4,998,881 A | 3/1991 | Lauks |
| 5,350,297 A * | 9/1994 | Cohen ...................... A61C 8/00 433/173 |

(Continued)

FOREIGN PATENT DOCUMENTS

| CN | 103156692 A | 6/2013 |
| CN | 103260542 A | 8/2013 |

(Continued)

OTHER PUBLICATIONS

International Search Report for PCT/SE2014/050968 dated Dec. 11, 2014.

(Continued)

*Primary Examiner* — Nicholas Lucchesi
*Assistant Examiner* — Shannel Wright
(74) *Attorney, Agent, or Firm* — Alston & Bird LLP

(57) ABSTRACT

The invention concerns a dental surgery device (1), comprising a punching member (15) having a cutting end part (16) suitable for removal of tissue on a jaw bone of a patient, and a guiding sleeve (7) for guiding the punching member (15) during a punching operation. The guiding sleeve (7) has a first side (8) intended to face away from the jaw bone and a second side (9) intended to face towards the jaw bone during a punching operation, and a guiding through-hole (101) extends from the first side (8) to the second side (9). The punching member (15) is adapted to fit into the guiding through-hole (101) such as to allow guidance by the guiding sleeve (7) when the punching member (15) is moved in an (Continued)

axial direction through the guiding through-hole (101). The invention is characterized in that the punching member (15) and the guiding sleeve (7) are provided with complementary guiding means configured to control the axial movement of the punching member (15) through the guiding through-hole (101) during the punching operation, wherein the complementary guiding means comprise at least one guiding element (17) that extends in a radial direction and at least one guiding groove (18) adapted to receive the guiding element (17) and guide its movement along the guiding groove (18), wherein the guiding groove (18) extends both in a circumferential direction as well as in an axial direction such that, when the guiding element (17) and the guiding groove (18) are engaged, a rotation of the punching member (15) in relation to the guiding sleeve (7) forces the punching member (15) to move in relation to the guiding sleeve (7) in the axial direction thereof.

19 Claims, 9 Drawing Sheets

(51) Int. Cl.
*A61B 17/3205* (2006.01)
*A61C 8/00* (2006.01)
*A61B 17/16* (2006.01)
*A61B 17/32* (2006.01)

(52) U.S. Cl.
CPC .............. *A61C 3/02* (2013.01); *A61C 8/0089* (2013.01); *A61B 17/1673* (2013.01); *A61B 2017/320052* (2013.01)

(58) Field of Classification Search
USPC .......................................................... 433/75
See application file for complete search history.

(56) References Cited

U.S. PATENT DOCUMENTS

| | | | |
|---|---|---|---|
| 5,488,958 A * | 2/1996 | Topel | A61B 17/320016 600/567 |
| 5,743,916 A | 4/1998 | Greenberg et al. | |
| 5,782,853 A * | 7/1998 | Zeevi | A61B 17/32053 30/329 |
| 6,110,178 A * | 8/2000 | Zech | A61B 17/1635 606/96 |
| 6,146,385 A * | 11/2000 | Torrie | A61B 17/1635 606/80 |
| 6,514,258 B1 | 2/2003 | Brown et al. | |
| 6,916,322 B2 * | 7/2005 | Jesch | A61B 17/1637 433/165 |
| 6,942,669 B2 | 9/2005 | Kurc | |
| 6,971,877 B2 * | 12/2005 | Harter | A61C 1/084 433/75 |
| 7,942,668 B2 | 5/2011 | Brajnovic et al. | |
| 8,777,613 B2 * | 7/2014 | Wolf | A61C 8/0089 433/76 |
| 8,794,963 B2 * | 8/2014 | Lancieux | A61C 1/084 433/75 |
| 9,211,126 B2 * | 12/2015 | Sikora | A61B 17/1604 |
| 9,615,841 B2 | 4/2017 | Eder | |
| 2004/0219479 A1 | 11/2004 | Malin et al. | |
| 2004/0219480 A1 * | 11/2004 | Malin | A61C 1/084 433/75 |
| 2004/0219481 A1 | 11/2004 | Malin et al. | |
| 2004/0236214 A1 * | 11/2004 | Opie | A61B 17/00008 600/434 |
| 2005/0170311 A1 | 8/2005 | Tardieu et al. | |
| 2006/0291968 A1 | 12/2006 | Greenberg | |
| 2007/0203500 A1 | 8/2007 | Gordon et al. | |
| 2008/0177266 A1 * | 7/2008 | Metcalf | A61B 17/025 606/80 |
| 2008/0220390 A1 | 9/2008 | Klein | |
| 2009/0181340 A1 | 7/2009 | Wolf et al. | |
| 2010/0062389 A1 | 3/2010 | Drews et al. | |
| 2010/0129768 A1 * | 5/2010 | Isidori | A61B 17/176 433/75 |
| 2010/0151412 A1 | 6/2010 | Suter et al. | |
| 2010/0311006 A1 | 12/2010 | Lancieux et al. | |
| 2011/0054483 A1 * | 3/2011 | Howlett | A61B 17/1617 606/96 |
| 2011/0059419 A1 | 3/2011 | Fujii | |
| 2011/0177469 A1 * | 7/2011 | Suter | A61C 8/0089 433/75 |
| 2011/0256500 A1 | 10/2011 | Crudo | |
| 2011/0270236 A1 * | 11/2011 | Eder | A61B 17/1673 606/3 |
| 2012/0067189 A1 * | 3/2012 | Kraft | B21D 28/34 83/698.91 |
| 2012/0109140 A1 | 5/2012 | Akutsu | |
| 2013/0084540 A1 | 4/2013 | Yoshihara et al. | |
| 2013/0157219 A1 | 6/2013 | Lo et al. | |
| 2013/0344453 A1 * | 12/2013 | Eder | A61B 17/176 433/29 |
| 2014/0046123 A1 * | 2/2014 | Connors | A61F 2/0027 600/31 |
| 2015/0342680 A1 * | 12/2015 | Schneider | A61B 18/24 606/14 |

FOREIGN PATENT DOCUMENTS

| | | | | |
|---|---|---|---|---|
| EP | 1759658 A1 | 3/2007 | | |
| EP | 2572671 A1 | 3/2013 | | |
| EP | 2381857 B1 | 7/2013 | | |
| ES | 1069431 U | 3/2009 | | |
| JP | 2009-207659 A | 9/2009 | | |
| WO | WO 2004/098435 A2 | 11/2004 | | |
| WO | WO 2004098435 A2 * | 11/2004 | ............ | A61C 1/082 |
| WO | WO 2007/065978 A1 | 6/2007 | | |
| WO | WO 2009/071885 A1 | 6/2009 | | |
| WO | WO 2010/049031 A | 5/2010 | | |

OTHER PUBLICATIONS

European Patent Office, Extended European Search Report for Application No. 14840347.0, dated Feb. 21, 2017, 5 pages, Germany.
The International Bureau of WIPO, International Preliminary Report on Patentability for International Application No. PCT/SE2014/050968, dated Mar. 1, 2016, 5 pages, Germany.
State Intellectual Property Office of the P.R.C., First Office Action, including Search Report, for Application No. 201480047132.8, dated Nov. 28, 2017, 13 pages, China.

* cited by examiner

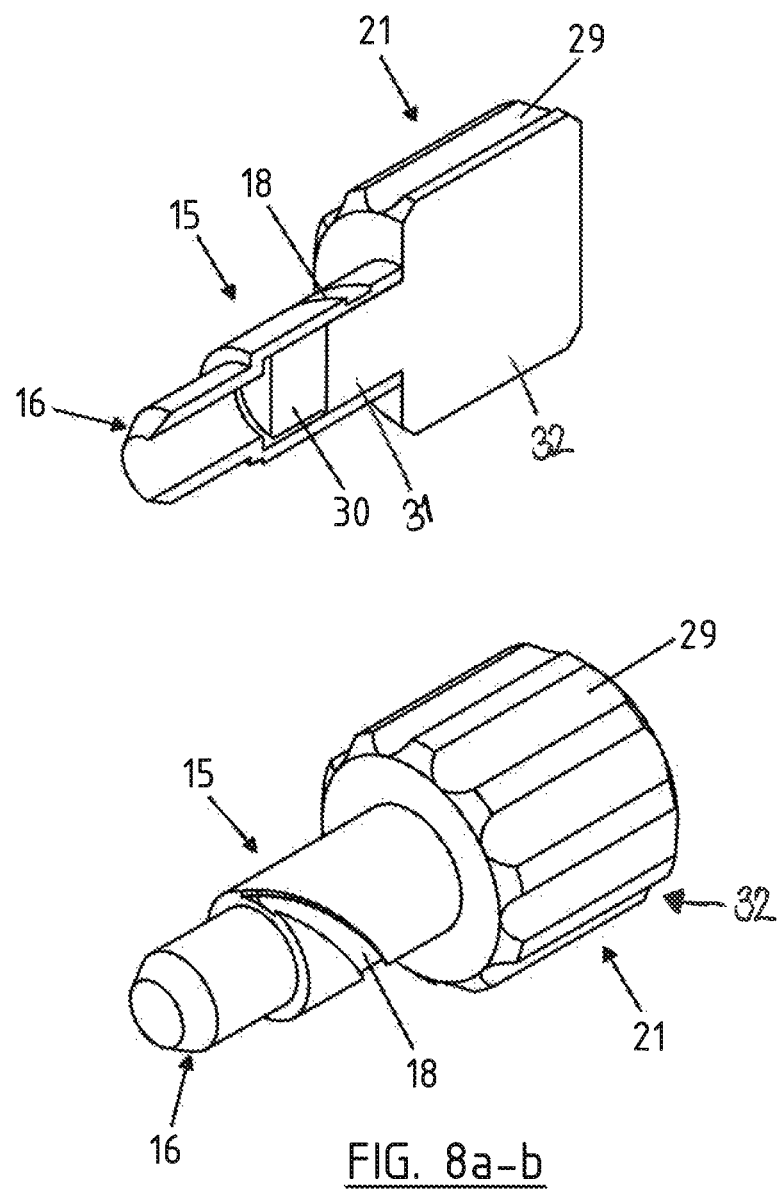
FIG. 8a-b

DENTAL SURGERY DEVICE

CROSS REFERENCE TO RELATED APPLICATIONS

This application is a U.S. National Phase Application of PCT International Application Number PCT/SE2014/050968, filed on Aug. 25, 2014, designating the United States of America and published in the English language, which is an International Application of and claims the benefit of priority to Swedish Patent Application No. 1350974-0, filed on Aug. 26, 2013. The disclosures of the above-referenced applications are hereby expressly incorporated by reference in their entireties.

TECHNICAL FIELD

This invention relates to a dental surgery device comprising a punching member having a cutting end part suitable for removal of tissue on a jaw bone of a patient, and a guiding sleeve for guiding the punching member during a punching operation, wherein the guiding sleeve has a first side intended to face away from the jaw bone and a second side intended to face towards the jaw bone during a punching operation, and wherein a guiding through-hole extends from the first side to the second side and wherein the punching member is adapted to fit into the guiding through-hole such as to allow guidance by the guiding sleeve when the punching member is moved in an axial direction through the guiding through-hole.

BACKGROUND

Dental surgery, such as replacing a tooth with an implant is commonly complicated and involves many steps and procedures. Once the old tooth is removed the replacement with an implant commonly involve the steps of making a gypsum or plastic model of the adjacent teeth i.e. a stent, arranging a guide in the stent, punching the gum tissue to expose the jawbone in the area of the missing tooth, placing the stent with the drill guide over the exposed area and drilling a hole into the bone in which the implant is to be arranged and installing the implant or an anchoring member. The actual crown, such as a prosthetic tooth or a bridge, is typically arranged into the implant or anchoring member several months later once the gum and bone have healed. Hence, it is beneficial if the punched hole is as tight around the upcoming drilling hole as possible such that less stitching and healing is needed. It is also preferred if the drilling itself is as accurate and as possible to minimize the impact on the tissue and the bone.

Commonly the punching or cutting of the tissue is done by hand and the punching is therefore relatively uncontrolled. The punch is immediately removed after punching, taking the punched gum with it. Thereafter the drilling is performed.

WO04/098435 discloses a method for arranging a drill bushing in a stent. The drill bushing may also function as a guide for aligning a tissue puncher. This makes the punching more controlled than if punching was done entirely by hand. However, there is still a need for improvements regarding the control of the punching.

Also, a lot of different tools are generally needed during dental surgery and there is a need for improved systems which comprise fewer tools with fewer individual parts in order to simplify the procedure for the dental surgeon.

There is also a need for more accurate tools which generates less damage during the procedure by improved control mechanisms.

SUMMARY OF THE INVENTION

An object of the invention is to provide an improved dental surgery device which facilitates controlled punching in dental surgery and which is also simple to use. This object is achieved by the device defined in claim 1.

The invention concerns a dental surgery device, comprising a punching member having a cutting end part suitable for removal of tissue on a jaw bone of a patient, and a guiding sleeve for guiding the punching member during a punching operation. The guiding sleeve has a first side intended to face away from the jaw bone and a second side intended to face towards the jaw bone during a punching operation, and a guiding through-hole extends from the first side to the second side. The punching member is adapted to fit into the guiding through-hole such as to allow guidance by the guiding sleeve when the punching member is moved in an axial direction through the guiding through-hole.

The invention is characterized in that the punching member and the guiding sleeve are provided with complementary guiding means configured to control the axial movement of the punching member through the guiding through-hole during the punching operation. The complementary guiding means comprise at least one guiding element that extends in a radial direction and at least one guiding groove adapted to receive the guiding element and guide its movement along the guiding groove, and the guiding groove extends both in a circumferential direction as well as in an axial direction such that, when the guiding element and the guiding groove are engaged, a rotation of the punching member in relation to the guiding sleeve forces the punching member to move in relation to the guiding sleeve in the axial direction thereof.

Thus, the interaction between the guiding element and the guiding groove during rotation of the punching member forces the punching member to move axially through the guiding through-hole. While the guiding sleeve controls the alignment of the punching member, the inventive device also provides means for controlling the axial movement of the punching member. To control the rotation of the punching member, and thereby indirectly control its axial movement, is easier than to directly control the axial movement of the punching member. This way it becomes easier to control the depth of the punching and deviated punching is minimized.

By giving the outer end of the punching member, i.e. the non-cutting end part, a suitable form for gripping, or by using a specially adapted tool connectable to the punching member, it is possible to achieve a very distinct but at the same time thoroughly controlled axial movement that provides for an efficient punching operation. The punching member can be moved in the opposite direction simply by rotating it in the opposite direction. That way, the punching member can also be removed from the guiding sleeve after use.

The guiding sleeve is typically adapted to be removably incorporated into a stent, i.e. a dental imprint of the teeth adjacent the site of the intended dental surgery, thereby holding the guiding sleeve in position. Thus, the guiding sleeve may have means for fastening it in a stent along its outer periphery.

The cutting end part of the punching member typically comprises means for cutting through tissue such that the jaw bone is exposed. Examples include but are not limited to a continuous sharp edge or a saw toothed edge.

The at least one guiding element may extend in a radial direction either from an inside of the guiding sleeve, if arranged onto the guiding sleeve, or from an outside of the punching member, if arranged onto the punching member. In this aspect the at least one guiding groove is arranged either on an outer side of the punching member, if the guiding element is arranged onto the guiding sleeve, or on the inside of the guiding sleeve, if the guiding element is arranged onto the punching member. Further, the guiding groove extends circumferentially and axially along the part it is arranged to.

The guiding element may preferably be in the form of a pin, which makes fitting of the guiding element into the guiding groove simple and also reduces the structural complexity. The complementary guiding means may comprise two or more guiding elements, preferably circumferentially distributed, and two or more corresponding guiding grooves. Other types of complementary guiding means are also possible e.g. the guiding element may be threaded wherein the thread is adapted to engage in a guiding groove slot which is complementary threaded.

The groove may be a recess or an opening extending radially through the entire wall of the member on which it is arranged, at least with regard to the punching member.

Preferably, the guiding sleeve is provided with the guiding element and the punching member with the guiding groove. One benefit with such a design is that it is less complicated to provide a guiding recess at the outside of the punching member than on the inside of the guiding sleeve. Such a punching member may also be used without the complementary guiding sleeve because it does not comprise any protruding guiding elements.

A pin-shaped elongated element may be arranged to extend in radial direction through a hole arranged through the guiding sleeve such that a tip of the pin-shaped elongated element protrudes on the inside of the guiding sleeve, i.e. it protrudes in the guiding through-hole, wherein said tip forms the guiding element. An advantage of such a design is that it is relatively easy to provide a wall of the guiding sleeve body with a radially extending hole and subsequently relatively easy to arrange a pin-shaped elongated element through such a hole.

The pin-shaped elongated element may be a screw and the hole in the guiding sleeve threaded thereby allowing the screw to be easily and securely arranged in the hole.

The guiding groove may have an open end that allows introduction of the guiding element into the guiding groove. The open end thus facilitates the fitting of the punching member in the guiding sleeve and enables the rotational movement to start.

The guiding groove may have a closed end that prevents further movement of the guiding element along the guiding groove. The closed end of the guiding groove thus prevents further rotation and axial movement of the punching member and thus defines an axial end position for the punching member relative the guiding sleeve. The depth of the punched hole may therefore be controlled.

The invention may be further improved by providing the guiding groove adjacent the closed end with an additional extension that extends in a different direction compared to the part of the guiding groove adjacent this additional extension, i.e. the guiding groove is subjected to a change in vertical and/or horizontal direction of extension. Thereby, the axial end position of the punching member is easily identified by a change in rotational movement of the punching member facilitated by the guiding element sliding into the additional extension of the guiding groove. An example of such an additional extension is obtained by providing the guiding groove with a distinct bend so that the additional extension of the guiding groove extends only in the circumferential direction. Such an exemplified additional extension defines at the bend an axial end position for the punching member relative the guiding sleeve, but the relative rotation can continue somewhat until the guiding element reaches the closed end.

The additional extension adjacent the closed end also facilitates that the punching member remains in its end position until a deliberate motion displaces it from the axial end position by moving the guiding element out of the additional extension of the closed end.

Alternatively, the depth of the punched hole can be controlled by providing the device with another element that defines an end position for the punching member. For instance, this can be arranged by providing a flange inside the guiding through hole that interacts with a corresponding surface or flange of the punching member, or by providing a flange on the outer end of the punching member that interacts with the first side of the guiding sleeve thereby defining the punching members end position.

The punching member preferably has a general shape of a circular cylinder.

The punching member may be hollow with a through-hole extending in an axial direction, wherein the through-hole is adapted to guide a dental drill. The through-hole of the punching member may preferably be circular.

Such a design gives the dental surgery device double function, as the punching member may function both as a punch and as a drill guide sleeve. An advantage of this is that the punching member does not have to be removed from the guiding sleeve prior to drilling. In addition, the drill will be guided all the way through the gum tissue towards the jaw bone because the cutting end of the punching member extends through the gum tissue. Thereby the guiding of the drill is improved compared to a conventional drill guiding sleeve that does not guide through the gum.

A hollow punching member provided with a through hole may also have a flange arranged in the through-hole of the punching member, the flange being adapted to define an end position for a drill stop sleeve arranged onto a dental drill introduced through the punching member. Alternatively, the drill stop sleeve may interact with the outer end part of the punching member, thereby controlling the drill depth. However, a flange arranged in the through-hole of the punching member allows the punching member to receive the drill stop sleeve, thereby giving the system the advantage of facilitating the use of shorter drills for the same drill depths. Shorter drills are commonly easier to handle for the dental surgeons.

In addition, the stability of drilling is increased if the drill stop sleeve is received by the punching member provided with a flange defining the drill stop sleeve end position.

The punching member may be provided with a first and second circumferentially spaced engagement member intended for engagement with a rotational tool. The rotational tool is used to facilitate a controlled rotation of the punching member but the rotation may also be done by hand. The engagement members ensure that the rotational tool is securely fastened when being used. The engagement members are preferably arranged at an upper/outer end of the punching member opposite the cutting end part either on the inside of the through-hole of the punching member or on the outside of the punching member.

The dental surgery device may further comprise a rotational tool adapted to engage with the punching member. The rotational tool thus has complementary engagement means adapted to engage with the engagement members of the punching member.

BRIEF DESCRIPTION OF THE DRAWINGS

The present invention will now be described in detail with reference to the figures, wherein:

FIG. 4b shows a cross section view of the drill stop sleeve of FIG. 4a;

FIG. 8a shows a cross section view of the rotational tool engaged to the punching member according to FIG. 1; and FIG. 8b shows a perspective view of the rotational tool engaged to the punching member according to FIG. 1.

DETAILED DESCRIPTION OF THE DRAWINGS

Figure 1:
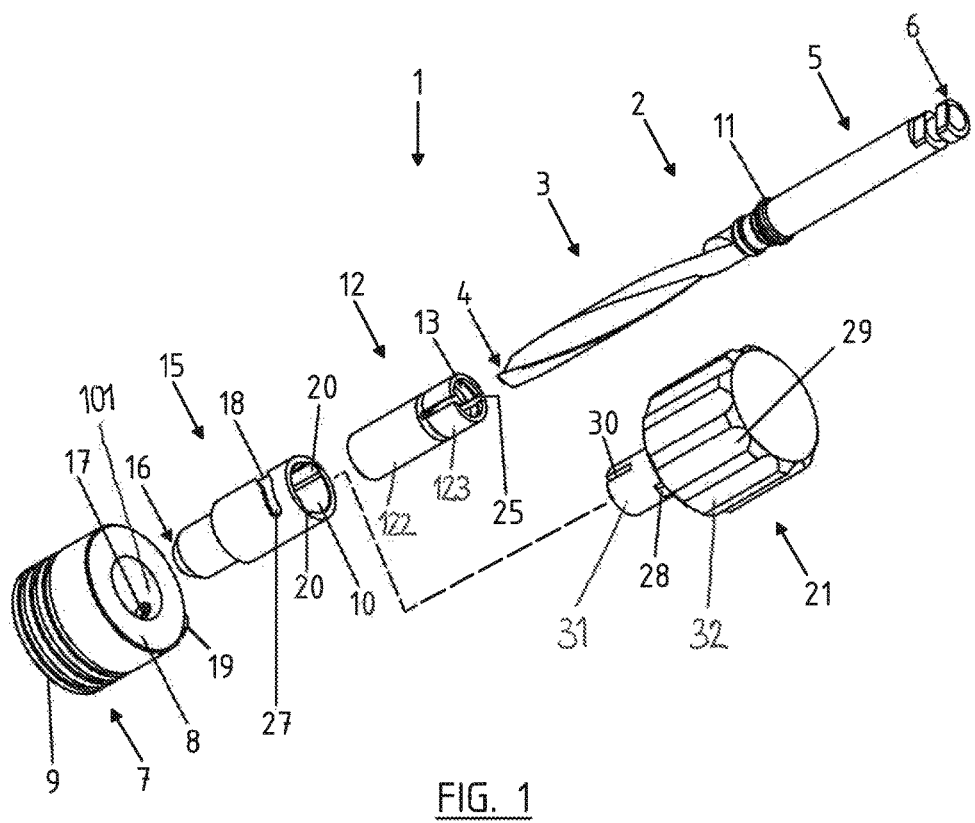
FIG. 1 shows an embodiment of a dental surgery device according to the invention.

FIG. 1 shows an example of a dental surgery device 1 according to the invention. The parts of the dental surgery device; a drill 2, a drill stop sleeve 12, a punching member 15, a guiding sleeve 7 and a rotational tool 21, are lined up in an exemplified order of assembly (before use). The drill 2 has a drilling part 3 with a first end 4 configured for drilling a hole in a jaw bone. The choice of drill diameter may be adapted to the situation, e.g. to the implant intended to be applied. The drill 2 also has a shank part 5 with a second end 6 configured for connection to a drill-rotating device. A rim 11 extends around the circumference of the shank part 5 of the drill 2. The rim 11 is positioned close to the drilling part 3 of the drill 2, i.e. closer to the drilling part 3 than to the second end of the shank part 5.

The drill stop sleeve 12 is of cylindrical shape and has a hollow interior extending through the length of drill stop sleeve 12. The drill stop sleeve 12 has a snap-lock part 123, comprising a recess 13 extending circumferentially around an inner side of the drill stop sleeve 12, and a sleeve part 122. The recess 13 is adapted to fit around the rim 11 of the drill 2. The sleeve part 122 is intended to extend circumferentially over the drilling part 3 of the drill 2 once the drill stop sleeve 12 has snap-locked upon the drill 2.

The drill stop sleeve 12 in FIG. 1 also has two cut outs 25 arranged circumferentially opposite each other extending perpendicular to the circumferential recess 13 going through the sleeve at the snap-lock part 123 of the drill stop sleeve 12. The cut outs 25 allow the snap-lock part 123 of the drill stop sleeve 12 to flex such that it may be brought over the rim 11 of the drill 2.

Figure 4B:
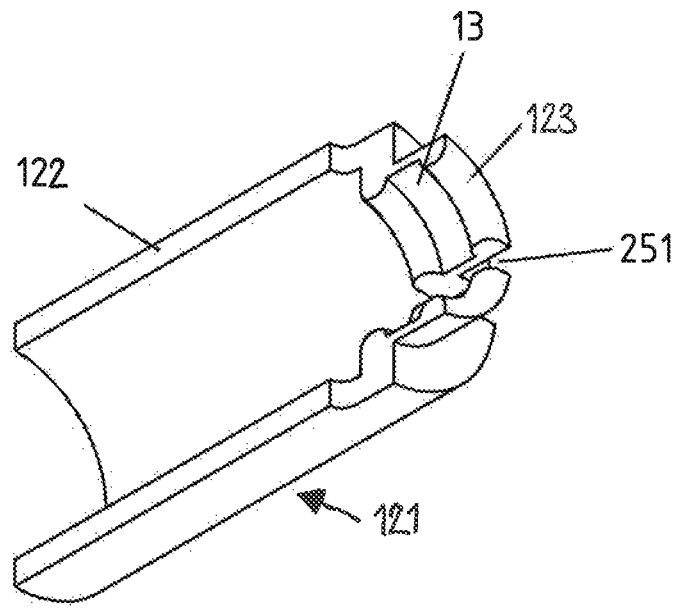
Figure 4A:
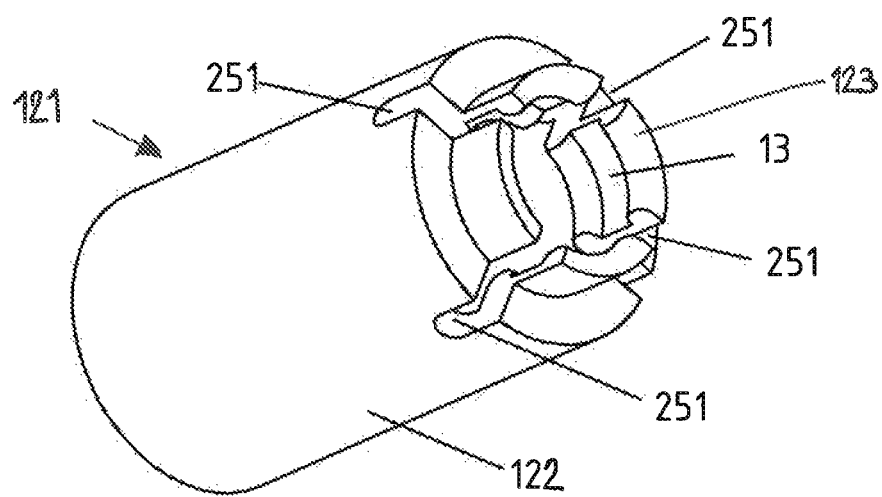
FIG. 4a shows a perspective view of an alternative drill stop sleeve.

Another example of a drill stop sleeve 121 in seen in FIG. 4a-b. The sleeve part 122 of the drill stop sleeve 121 has in this case a larger diameter than the snap-lock part 123 thereby enabling the sleeve part 122 to fit a drill 2 of a larger bore diameter, i.e. comprising a drilling part 3 which is wider than the shank part 5. The drill stop sleeve 121 is provided with four cut outs 251 evenly spaced along the circumference of the drill stop sleeve 121 such that the cut outs 251 are arranged in two pairs and wherein the cut-outs 251 of each pair are arranged opposite each other. The cut outs 251 extend from the edge of the snap-lock part 123 of the drill stop sleeve 121, across the snap-lock part 123 and towards the sleeve part 122 of the drill stop sleeve 121. The number of cut-outs 251 and the extension of the cut-outs 251 in vertical direction may of course vary.

During assembly the drill stop sleeve 12 may be brought onto the drill 2 from the second end 6 towards the drilling part 3 such that the snap-lock part 123 of the drill stop sleeve 12 snap-locks onto the drill 2 by allowing the recess 13 of the drill stop sleeve 12 to engage with the rim 11 on the shank part 5 of the drill 2. The diameter of the recess 13 and the diameter of the rim 11 are configured relative each other such that the drill stop sleeve 12 may be securely arranged to snap-lock upon the drill 2 and securely lock the position of the drill stop sleeve 12.

Figure 2:
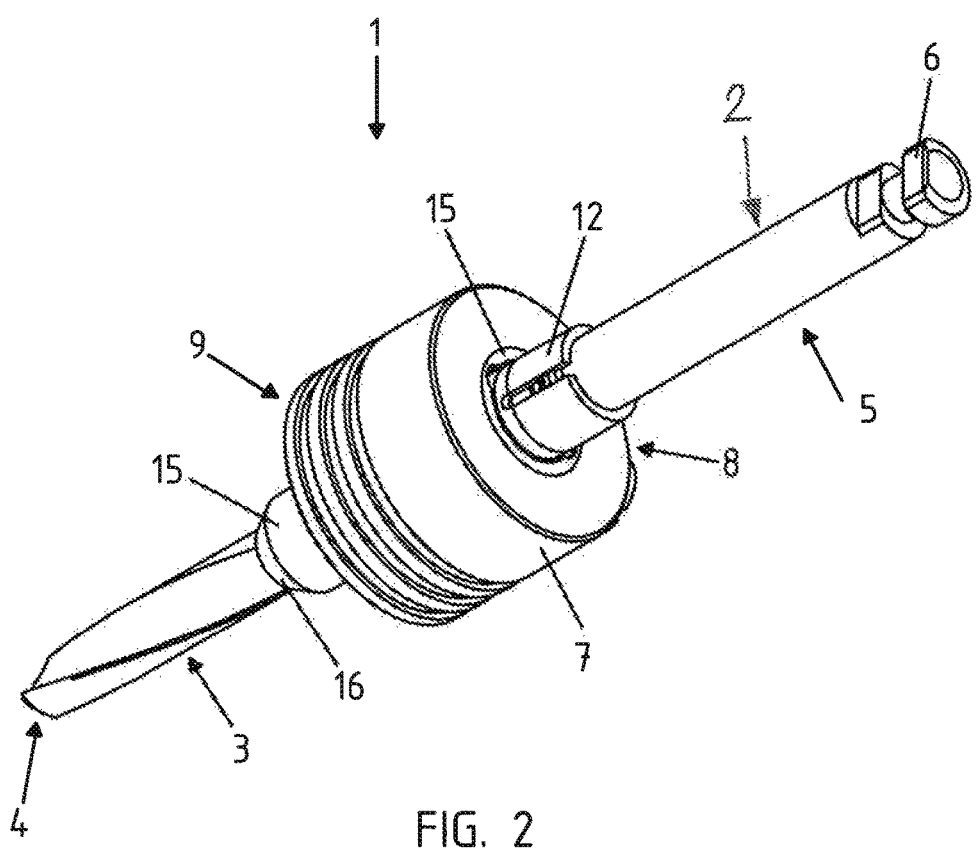
FIG. 2 shows the embodiment of FIG. 1 when assembled.
Figure 3:
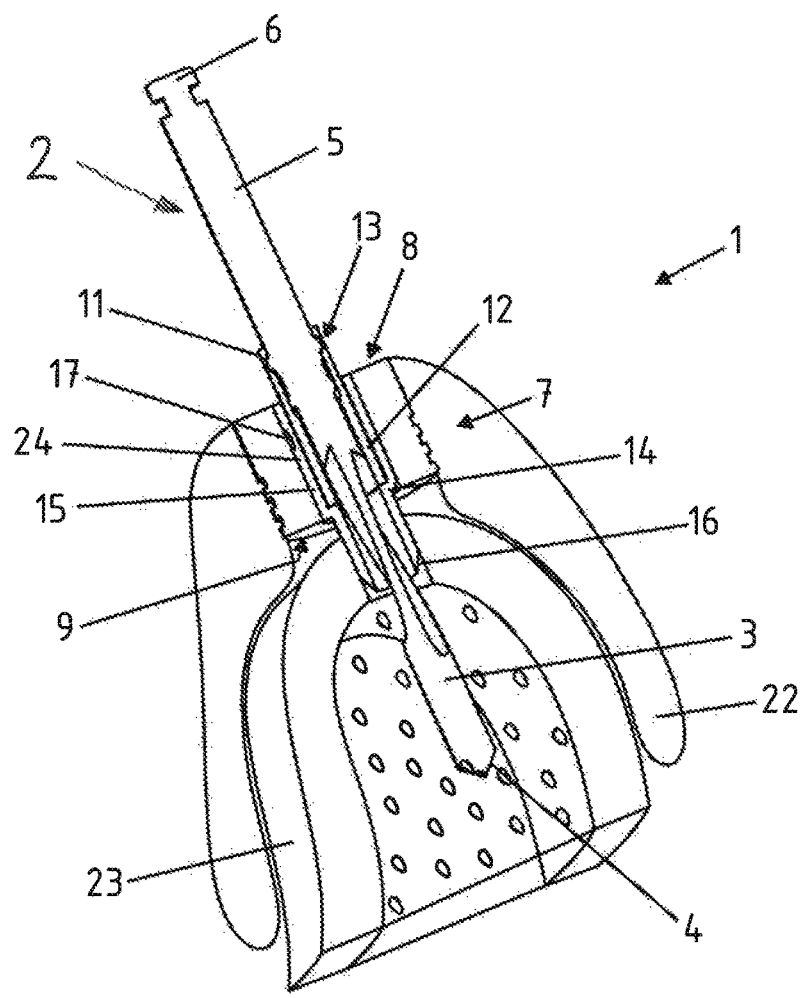
FIG. 3 shows a cross section of the embodiment of FIG. 1 when in use.

The punching member 15 has the shape of a hollow circular cylinder and is arranged to fit in the guiding sleeve 7. The punching member 15 is provided with a cutting part 16, intended to face the jaw bone during a punching operation, and a sleeve part 160. The diameter of the cutting part 16 is less than the diameter of the sleeve part 160. During use, the cutting part 16 protrudes from the second part 9 of the guiding sleeve 7 whereas the sleeve part 160 is arranged inside the guiding sleeve 7, as shown in FIGS. 2-3. The guiding sleeve 7 has a through-hole 101 with an inner diameter adapted to the outer diameter of the punching member 15.

Figure 5:
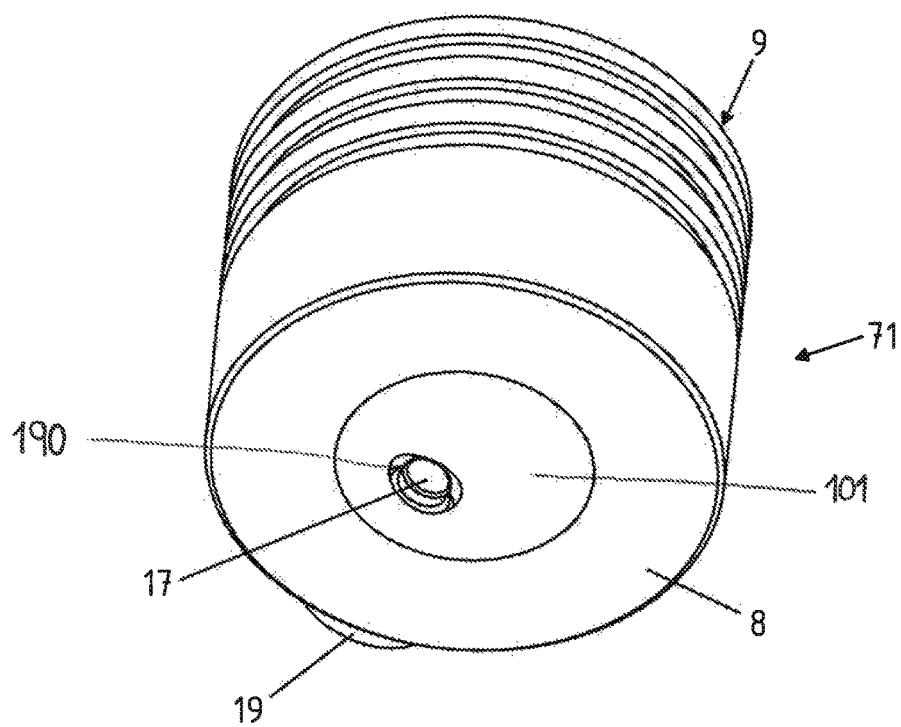
FIG. 5 shows a perspective view of the guiding sleeve of FIG. 1.

The guiding sleeve 7 is provided with a pin-shaped elongated element 19, in the form of a screw, which extends in a radial direction through a thread-provided, radial extending, hole 190 arranged through a wall of the guiding sleeve 7. The tip of the pin-shaped elongated element 19 protrudes on the inside of the guiding sleeve 7 such that it forms the guiding element 17, seen in FIG. 5. Thereby the guiding element 17 is easily arranged upon the guiding sleeve 7.

Figure 6A:
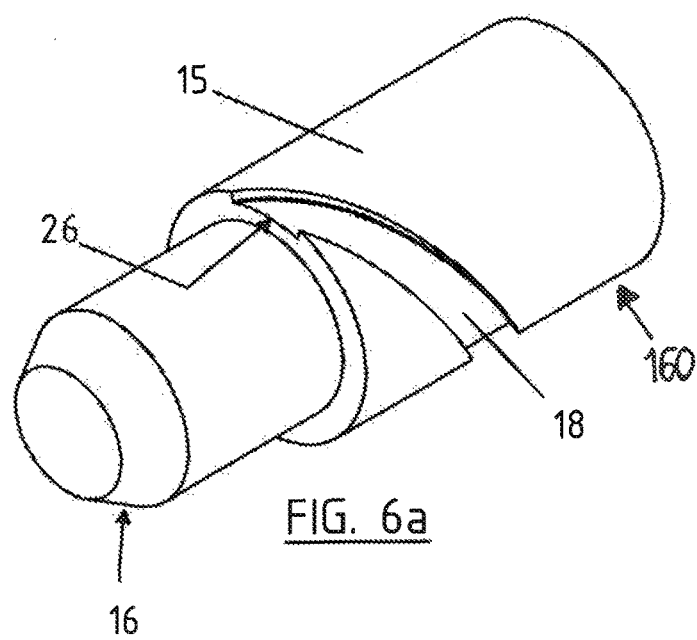
FIG. 6a-c shows a perspective view of the punching member of FIG. 1.
Figure 6B:
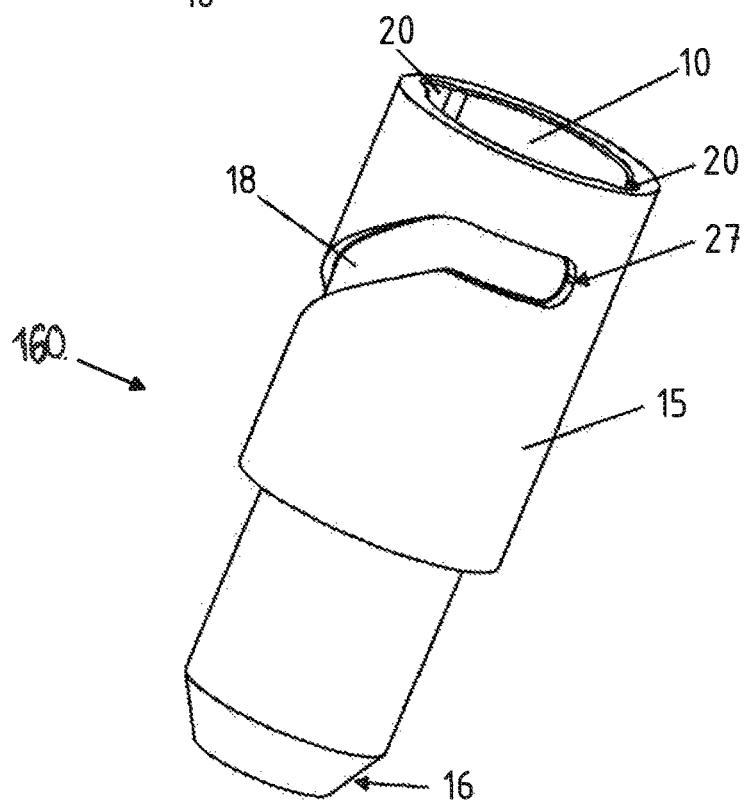

The punching member 15 is provided with a guiding groove 18 in the form of a recess that extends both in a circumferential direction as well as in an axial direction, in a helical manner, along the outer surface of the punching member 15, specifically on the sleeve part 160. The guiding groove 18 is provided with an open end 26 (see FIG. 6a) that allows introduction of a protruding pin-shaped elongated element 19 of the guiding sleeve 7 into the guiding groove 18 and a closed end 27 (see FIGS. 1 and 6b) that prevents further movement of the guiding element 17 along the guiding groove 18 upon rotational movement of the punching member 15 relative the guiding sleeve 7. The open end 26 of the guiding groove 18 is open towards the edge of the sleeve part 160 facing the cutting part 16. The guiding groove 18, starting from the open end 26, extends both in a circumferential direction as well as in an axial direction towards the closed end 27 with a pitch angle of about 30°. The exact angle and path of the guiding groove 18 may be adapted to the particular application.

A part, an additional extension, of the guiding groove 18 adjacent the closed end 27 is essentially horizontal, i.e. it extends only circumferentially and not axially such that the pitch angle becomes zero. Thereby, the axial movement of the punching member 15 relative the guiding sleeve 7 is stopped once the guiding pin 17 reaches the part adjacent the closed end 27 of the guiding groove 18. The punching member 15 may be left in this position, being the end position of the axial movement.

The movement of the guiding element 17 in the guiding groove 18, together making up the complementary guiding means, controls the axial movement of the punching member 15 relative the guiding sleeve 7, consequently controlling axial movement of the cutting edge 16 into the tissue. The angle and path of the guiding groove 18, together with the rotational speed and torque, thereby controls the punching operation.

When the punching member 15 is inserted into the guiding sleeve 7 it is rotationally adjusted so that the guiding element 17 i.e. the tip of the pin-shaped elongated element 19, enters the open end 26 of the guiding groove 18. When the punching member 15 at that point is rotated, e.g. by using the tool 21, the guiding element 17 will follow the path defined by the guiding groove 18. Since this path extends both circumferentially around the punching member 15 as well as axially towards its other end 27, i.e. in a helical movement, the punching member 15 is forced to move in the axial direction towards the second part 9 of the guiding sleeve 7. As the guiding element 17 reaches the horizontal additional extension of the guiding groove 18, i.e. adjacent the closed end 27, the axial movement stops. As the guiding element 17 reaches the closed end 27 of the guiding groove 18, further rotation is prevented.

Figure 6D:
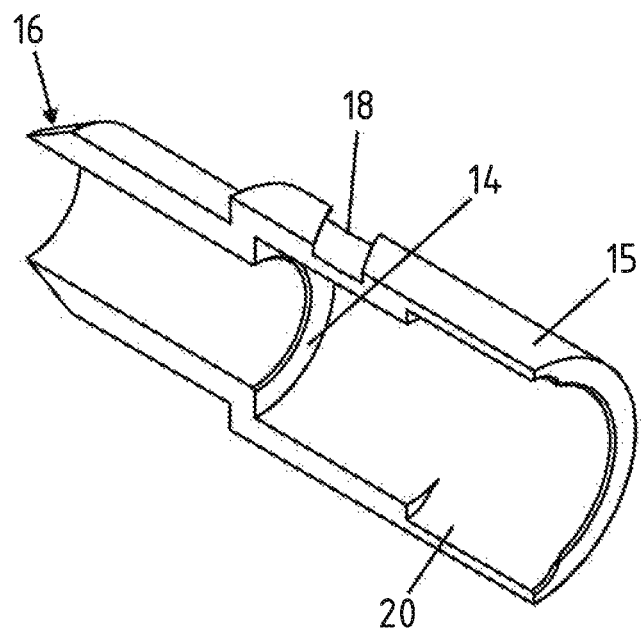
FIG. 6d shows a cross section view of the punching member of FIG. 6a-c.
Figure 6C:
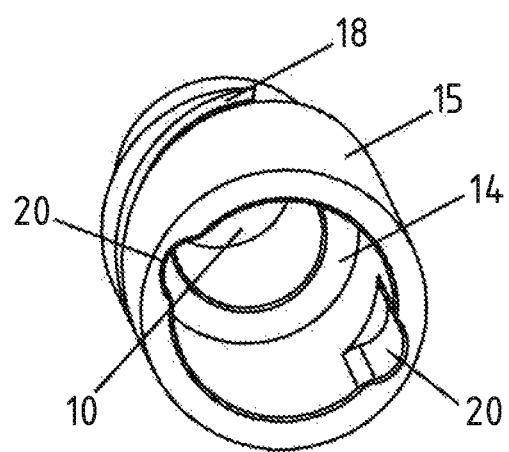

The punching member 15 is further provided with a guiding through-hole 10 that makes it capable of receiving and guiding the drill 2 (via the drill stop sleeve 12) during drilling operation, see FIGS. 2-3. Thereby, the punching member 15 has dual function. The diameter of the guiding through-hole 10 is adapted to the diameter of the drill stop sleeve 12 provided upon the drill 2. A flange 14, see FIGS. 6c-d, extends circumferentially along the inside of the guiding through-hole 10, wherein the flange 14 defines the end position of the drill stop sleeve 12 in the guiding through-hole 10.

The flange 14 defines the axial end of a portion 24 of the guiding through-hole 10, i.e. it determines the depth of the portion 24 of the punching member 15. The maximum possible protrusion of the drilling part 3 of the drill 2 from the punching member 15 is reached when the drill stop sleeve 12 abuts the flange 14, and hence the drilling depth may be controlled by the punching member 15 arranged in the guiding sleeve 7.

The punching member 15 is also provided with a first and a second circumferentially spaced engagement member 20, wherein each engagement member 20 is a groove arranged on the inside of the guiding through-hole 10 extending axially from the outer end of the punching member 15, and intended for engagement with complementary engagement means 28 of the rotational tool 21. The rotational tool 21 is used to provide a lever that reduces the force needed to rotate the punching member 15 in the guiding sleeve 7. This enhances the control of the axial movement of the punching member 15.

Figure 7:
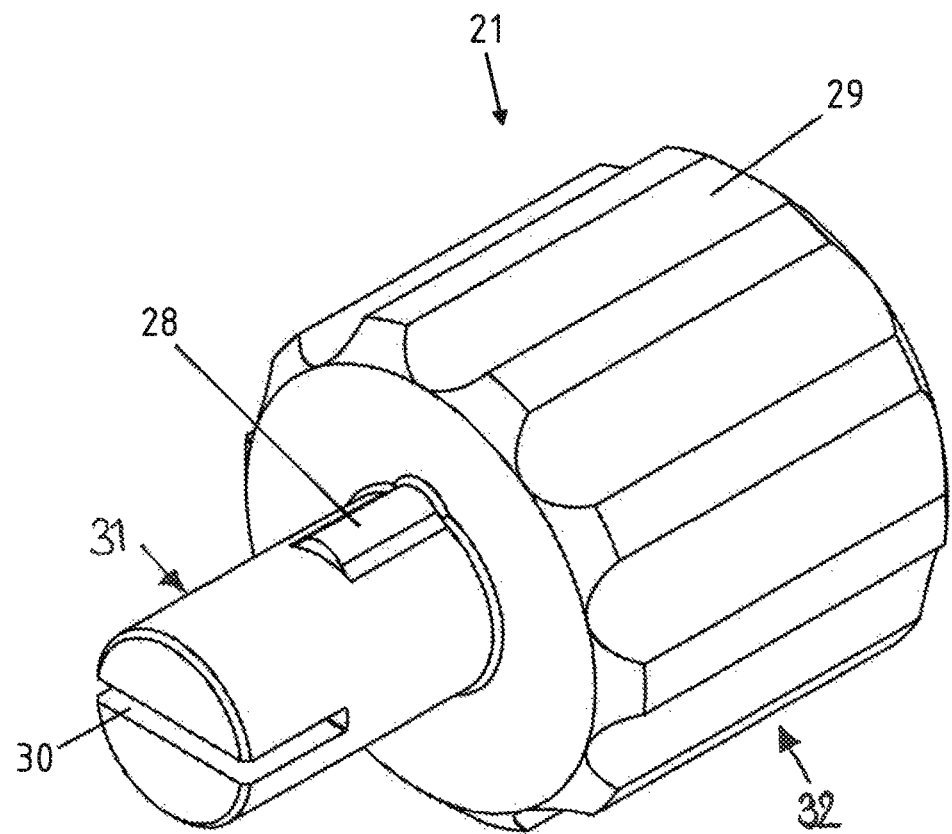
FIG. 7 shows a perspective view of the rotational tool of FIG. 1.

The rotational tool 21 seen in FIGS. 1, 7 and 8 has a first part 31 and a second part 32, wherein the first part 31 is cylindrical and the diameter is adapted such that the first part 31 fits inside the through-hole 10 of the punching member 15, as seen in FIG. 8a-b. The outer diameter of the first part 31 of the rotational tool 21 is essentially equal the inner diameter of the through-hole 10 such that the first part 31 of the rotational tool 21 may be received by the guiding through-hole 10 of the punching member 15. The first part 31 of the rotational tool 21 is provided with engagement means 28, shown as circumferentially spaced ridges extending perpendicular to the circumference of the first part 31 of the rotational tool 21. The engagement means 28 are spaced at the same distance as, and adapted to engage with, the engagement members 20 of the punching member 15. The free end of the first part 31 of the rotational tool 21 is further provided with a cut out 30 arranged across the cylinder diameter and extending in axial direction about half the length of the cylinder, thereby allowing the first part 31 of the rotational tool 21 to flex its diameter such that it may easily enter into the guiding through-hole 10 of the punching member 15. Thereby a rotation of the rotational tool 21 facilitates rotation of the punching member 15 relative the guiding sleeve 7.

The second part 32 has a larger diameter than the first part 31 of the rotational tool 21 and is provided with a cylindrically shaped knob facilitating manual gripping. The knob is provided with rills 29 perpendicular to its circumference which facilitates a good grip upon manual rotation of the rotational tool 21. The knob may of course be of other suitable shapes or provided with other patterns which facilitate gripping and thereby simplify the rotation of the rotational tool 21.

FIG. 2 shows the dental surgery device 1 in an assembled state wherein the drill 2, with the drill stop sleeve 12 snap-locked onto it, is arranged through the punching member 15 which has been positioned in its end position in the through-hole 101 of the guiding sleeve 7 i.e. it has been guided by complementary guiding means through the guiding sleeve 7 as described in detail above. The cutting end part 16 of the punching member 15 extends from the second side 9 of the guiding sleeve 7.

FIG. 3 shows the dental surgery device 1 in use; arranged in a stent 22 which is arranged upon a drilling site in a patient's mouth. The mantle surface of the guiding sleeve 7 is provided with a retention profile shown as threads (also seen in FIG. 5) which facilitate arrangement of the guiding sleeve 7 in the stent. The cutting end part 16 of the punching member 15 protrudes from the second side 9 of the guiding sleeve 7 and extends through the gum tissue 23 exposing the jaw bone 22 of a patient when in its end position, i.e. at its end axial position defined by the complementary guiding means. The outer part of the punching member 15, opposite the cutting end part 19, is arranged flush the first side 8 of the guiding sleeve 7.

The sleeve part 122 of the drill stop sleeve 12 is received in the guiding through-hole 10 in the punching member 15 such that it abuts the flange 14 arranged inside the guiding through-hole 10 of the punching member 15. The sleeve part 122 of the drill stop sleeve 12 is extending over the drilling part 3 of the drill 2. Thereby, the length of the sleeve part 122 determines the drilling depth of the exemplified drill 2. Part of the drilling part 3 of the drill 2 is protruding from the punching member 15, entering the jaw bone. Thereby the punching member 15 functions also as a guide for the drill 2 during drilling operation.

The individual parts of the dental surgery device 1 may be disassembled into separate parts, i.e. drill 2, drill stop sleeve 12, punching member 15 and guiding sleeve 7 after use. The individual parts may be reused, preferably after being autoclaved. The individual parts may be used separately.

The invention is not limited to the specific embodiment presented, but includes variations within the scope of the present claims. The guiding element may for example be a pin, a continuous thread, a broken thread or any other element suitable for being guided in a guiding groove. The elongated pin-shaped element may be a screw, a nail or any other suitable through-going element.

The term sleeve is considered to encompass various kinds of hollow cylinders.

The closed end of the guiding groove and the additional extension of the guiding groove adjacent the closed end may be arranged as a distinct bend in the guiding groove, e.g. forming a 90° pitch angle such that the end of the guiding groove extends only axial. It may also form a 180° angle such that it extends only circumferentially in a direction opposite the circumferential extension of the guiding groove. Other patterns that make up the final position in the guiding groove for the guiding element are also possible.

The axial end position of the punching member can alternatively, or as a complement, be arranged by designing the punching member and the guiding sleeve so that further axial movement is prevented by the first side of the guiding sleeve or by a flange arranged inside the guiding sleeve.

The term punching member is considered to encompass different kinds of punching elements adapted to fit in the guiding sleeve and provided with a cutting end part. For instance, the punching member does not necessarily need to be provided with a through-hole for guiding a drill or drill stop. The punching member exemplified above may also be called punching sleeve.

Reference signs mentioned in the claims should not be seen as limiting the extent of the matter protected by the claims, and their sole function is to make claims easier to understand.

As will be realised, the invention is capable of modification in various obvious respects, all without departing from the scope of the appended claims. Accordingly, the drawings and the description thereto are to be regarded as illustrative in nature, and not restrictive.

The invention claimed is:

1. A dental surgery device, comprising:
    a punching member having a cutting end part suitable for removal of tissue on a jaw bone of a patient, and
    a guiding sleeve for guiding the punching member during a punching operation,
    wherein:
        the guiding sleeve has a first side intended to face away from the jaw bone and a second side intended to face towards the jaw bone during a punching operation, and wherein a guiding through-hole extends from the first side to the second side,
        the punching member is configured to fit into the guiding through-hole such as to allow guidance by the guiding sleeve when the punching member is moved in an axial direction through the guiding through-hole,
        the punching member and the guiding sleeve are provided with a complementary guide configured to control the axial movement of the punching member through the guiding through-hole during the punching operation,
        the complementary guide comprises a guiding element that extends in a radial direction and a single guiding groove that receives the guiding element and guides the guiding element's movement along the single guiding groove,
        the guiding element extends in the radial direction either from an inside of the guiding sleeve, if arranged onto the guiding sleeve, or from an outside of the punching member, if arranged onto the punching member,
        the single guiding groove is arranged either on an outer side of the punching member, if the guiding element is arranged onto the guiding sleeve, or on the inside of the guiding sleeve, if the guiding element is arranged onto the punching member, and
        the single guiding groove consists of an open end, a first portion extending both circumferentially and axially, and a second portion extending in a circumferential direction, the first portion being located intermediate the open end and the second portion, such that, when the guiding element and the single guiding groove are engaged, a rotation of the punching member in relation to the guiding sleeve forces the punching member to move in relation to the guiding sleeve in the axial direction thereof.

2. The dental surgery device according to claim 1, wherein the guiding sleeve is provided with the guiding element and the punching member is provided with the single guiding groove.

3. The dental surgery device according to claim 2, wherein a pin-shaped elongated element is arranged to extend in radial direction through a hole arranged through the guiding sleeve such that a tip of the pin-shaped elongated element protrudes on the inside of the guiding sleeve, wherein said tip forms the guiding element.

4. The dental surgery device according to claim 3 wherein the pin-shaped elongated element is a screw.

5. The dental surgery device according to claim 1, wherein the open end is configured to allow introduction of the guiding element into the single guiding groove.

6. The dental surgery device according to claim 1, wherein the second portion of the single guiding groove defines, in part, a closed end that prevents further movement of the guiding element along the guiding groove.

7. The dental surgery device according to claim 1, wherein the punching member has a general shape of a circular cylinder.

8. The dental surgery device according to claim 1, wherein the punching member is hollow with a through-hole extending in an axial direction, wherein the through-hole is adapted to guide a dental drill.

9. The dental surgery device according claim 8 wherein a flange is arranged in the through-hole of the punching member, wherein the flange is configured to define an end position for a drill stop sleeve arranged onto a dental drill introduced through the punching member.

10. The dental surgery device according to claim 1, wherein the punching member is provided with a first and a second circumferentially spaced engagement member intended for engagement with a rotational tool.

11. The dental surgery device according to claim 1, further comprising a rotational tool configured to engage with the punching member.

12. The dental surgery device according to claim 1, wherein the single guiding groove extends for less than one revolution about the complementary guide.

13. The dental surgery device according to claim 1, wherein the first portion is oriented at a first pitch relative to the complementary guide and the second portion is oriented at a second pitch relative to the complementary guide, the second pitch being different from the first pitch.

14. The dental surgery device according to claim 13, wherein the first pitch is 30°.

15. The dental surgery device according to claim 13, wherein the second pitch is 0°.

16. A dental surgery device, comprising:

a punching member having a cutting end part suitable for removal of tissue on a jaw bone of a patient, and a guiding sleeve for guiding the punching member during a punching operation, wherein:

the guiding sleeve has a first side intended to face away from the jaw bone and a second side intended to face towards the jaw bone during a punching operation, and wherein a guiding through-hole extends from the first side to the second side, the punching member is configured to fit into the guiding through-hole such as to allow guidance by the guiding sleeve when the punching member is moved in an axial direction through the guiding through-hole, the punching member and the guiding sleeve are provided with a complementary guide configured to control the axial movement of the punching member through the guiding through-hole during the punching operation, the complementary guide comprises at least one guiding element that extends in a radial direction and at least one guiding groove that receives the at least one guiding element and guides the at least one guiding element's movement along the at least one guiding groove, the at least one guiding element extends in the radial direction either from an inside of the guiding sleeve, if arranged onto the guiding sleeve, or from an outside of the punching member, if arranged onto the punching member, the at least one guiding groove is arranged either on an outer side of the punching member, if the at least one guiding element is arranged onto the guiding sleeve, or on the inside of the guiding sleeve, if the at least one guiding element is arranged onto the punching member, the at least one guiding groove consists of an open end, a first portion extending both circumferentially and axially, and a second portion extending in a circumferential direction, the first portion being located intermediate the open end and the second portion, such that, when the guiding element and the at least one guiding groove are engaged, a rotation of the punching member in relation to the guiding sleeve forces the punching member to move in relation to the guiding sleeve in the axial direction thereof; and the at least one guiding groove extends for less than two revolutions about the complementary guide.

17. The dental surgery device according to claim 16, wherein the guiding groove extends for less than one revolution about the complementary guide.

18. The dental surgery device according to claim 16, wherein the second portion of the at least one guiding groove defines, in part, a closed end.

19. The dental surgery device according to claim 16, wherein the first portion is oriented at a first pitch relative to the complementary guide and the second portion is oriented at a second pitch relative to the complementary guide, the second pitch being different from the first pitch.

* * * * *